US008623878B2

(12) United States Patent
Rodemer

(10) Patent No.: US 8,623,878 B2
(45) Date of Patent: Jan. 7, 2014

(54) USE OF ALLOPURINOL FOR THE TREATMENT OF HAND FOOT SKIN REACTION

(75) Inventor: Yolanda Rodemer, WilhemsHaven-Rustersiel (DE)

(73) Assignees: Nobera Pharma, S.L., Madrid (ES); Advancell Advanced In Vitro Cell Technologies, S.A., Barcelona (ES)

( * ) Notice: Subject to any disclaimer, the term of this patent is extended or adjusted under 35 U.S.C. 154(b) by 87 days.

(21) Appl. No.: 12/770,179

(22) Filed: Apr. 29, 2010

(65) Prior Publication Data

US 2010/0280051 A1 Nov. 4, 2010

Related U.S. Application Data

(60) Provisional application No. 61/214,894, filed on Apr. 29, 2009.

(30) Foreign Application Priority Data

Apr. 29, 2009 (EP) ..................................... 09382058

(51) Int. Cl.
*A01N 43/90* (2006.01)
*A61K 31/519* (2006.01)

(52) U.S. Cl.
USPC ....................................................... 514/262.1

(58) Field of Classification Search
USPC ....................................................... 514/262.1
See application file for complete search history.

(56) References Cited

U.S. PATENT DOCUMENTS

| | | | |
|---|---|---|---|
| 4,943,575 A | 7/1990 | Cremer | |
| 6,060,083 A | 5/2000 | Dorr et al. | |
| 6,419,913 B1 | 7/2002 | Niemiec et al. | |
| 6,685,917 B2 | 2/2004 | Rosenthal et al. | |
| 6,979,688 B2 | 12/2005 | Ford | |
| 2002/0119104 A1 | 8/2002 | Rosenthal et al. | |
| 2003/0060486 A1 | 3/2003 | Jacob et al. | |
| 2003/0157191 A1 | 8/2003 | Kil et al. | |
| 2004/0102524 A1* | 5/2004 | Hughes | 514/651 |
| 2004/0214215 A1 | 10/2004 | Yu et al. | |
| 2005/0142093 A1 | 6/2005 | Skover et al. | |
| 2006/0177374 A1 | 8/2006 | Curd et al. | |
| 2006/0178351 A1 | 8/2006 | Curd et al. | |

FOREIGN PATENT DOCUMENTS

| | | |
|---|---|---|
| DE | 102 00 578 A1 | 7/2003 |
| JP | 31-06817 | 5/1991 |
| JP | 2006-06700 | 2/2006 |
| WO | WO 94/05291 | 3/1994 |
| WO | WO 94/05293 * | 3/1994 |
| WO | WO 03/018102 A2 | 3/2003 |
| WO | WO 2004/110380 | 12/2004 |
| WO | WO 2006/030439 A | 3/2006 |
| WO | WO 2007/138103 * | 12/2007 |
| WO | WO 2007/138103 A1 | 12/2007 |

OTHER PUBLICATIONS

Lacouture et al. (Annals of Oncology 19; 1955-1961 (2008).*
Elworthy, J. Pharmacy and Pharmacology, 12(S1) 1960.*
Yancovitz et al Dermatology Online J. 14(10); 2008.*
Bhutani et al (Annals of Oncology 13:1833-1834 (2002).*
Huggins et al. (J Clin Oncol 26: 2008 (May 20 suppl; abstr 16122).*
Mayo Clinic (1998) and Mauro et al. (The Oncologist 2001;6:233-238).*
Feldman-J. Clinical oncology, (2009) 27(9) 1432-1439.*
Hammond-Thelin Dermtol. Clin 26 (2008)121-159.*
Anderson, R. et al., Search for Evidence-Based Approaches for the Prevention and Palliation of Hand-Foot Skin Reaction (HFSR) Caused by Multikinase Inhibitors (MKIs), The Oncologist, 2009, vol. 14, pp. 291-302.
Autier, J. et al., "Prospective Study of the Cutaneous Adverse Effects of Sorafenib, a Novel Multikinase Inhibitor", Arch. Dermatol., 2008, vol. 144, No. 7, pp. 886-892.
Azad, N. et al., "Hand-Foot Skin Reaction Increases with Cumulative Sorafenib Dose and with Combination Anti-Vascular Endothelial Growth Factor Therapy", Clinical Cancer Research, 2009, vol. 15, No. 4, pp. 1411-1416.
Beldner, M. et al., "Localized palmar-plantar epidermal hyperplasia: a previously undefined dermatologic toxicity to sorafenib", The Oncologist, 2007, vol. 12, No. 10, pp. 1178-118.
Chin, S.F., "Use of 'Bag Balm' as Topical Treatment of Palmar-Plantar Erythrodysesthesia Syndrome (PPES) in Patients Receiving Selected Chemotherapeutic Agents", Proc Am Soc Clin Oncol., 2001; 20: Abstract 1623.
Chu, D. and Lacouture, M.E., "Risk of hand-foot skin reaction with sorafenib: A systematic review and meta-analysis", Acta Oncologica, 2008, vol. 47, No. 2, pp. 176-186.
Chu, D. and Lacouture, M.E., "Risk of Hand-Foot Skin Reaction with Multitarged Kinase Inhibitor Sunitinib in Patients with Renal Cell and Non-Renal Cell Carcinoma: A Meta-Analysis", Clinical Genitourinary Cancer, 2009, vol. 7, No. 1, pp. 11-19.
Dagher G. et al., "Allopurinol Mouthwash and Vaginal Cream for 5-Fu-Induced Mucositis", Canadian Journal of Hospital Pharmacy, vol. 40, No. 5, 1987, p. 189, XP009075859 ISSN: 0008-4123.
El-on, J. et al., "Development of topical treatment for cutaneous Leishmaniasis Caused by *Leishmania-major* in Experimental Animals", Antimicrobial Agents and Chemotherapy, vol. 26, No. 5, 1984, pp. 745-751, XP009075856 ISSN: 0066-4804.
Gilbar, P., "Palmar-plantar erythrodysesthesia", Journal of Oncology Pharmacy Practice, 2003, vol. 9, No. 4, pp. 137-150, XP002410273 ISSN:10978-1552.

(Continued)

*Primary Examiner* — Shirley V Gembeh
(74) *Attorney, Agent, or Firm* — Gary J. Gershik; Cooper & Dunham LLP

(57) ABSTRACT

Use of allopurinol or a pharmaceutically acceptable salt thereof for the treatment or prevention of Hand Foot Skin Reaction (HFSR) induced by Multitargeted Kinase Inhibitor (MKI) therapy. The allopurinol or its salt is administered topically to the affected areas, palms and soles, preferably in the form of a cream.

19 Claims, No Drawings

(56) References Cited

OTHER PUBLICATIONS

Hanawa, T., "Development of patient-friendly preparations: preparation of a new allopurinol mouthwash containing polyethylene(oxide) and carrageenan", Drug Dev Ind Pharm., (2004); 30(2):151-61, Abstract.

Kitagawa, J. et al., "Allopurinol gel mitigates radiation-induced mucositis and dermatitis", Journal of Radiation Research, 2008, vol. 49, No. 1, pp. 49-54.

Kondratiev, V.B., "Complications induced by chemotherapy of colon cancer and methods for treatment thereof", Prakticheskaya Onkologica, 2000, No. 1, pp. 31-36.

Lacouture, M.E. et al., "Evolving strategies for the management of hand-foot skin reaction associated with the multitargeted kinase inhibitors sorafenib and sunitinib", The Oncologist, 2008, vol. 13, No. 9, pp. 1001-1011.

Lauman, M.K. et al., "Effect of Pyridoxine on the Incidence of Palmar Plantar Erythroderman (PPE) in Patients Receiving Capecitabine", Proc Am Soc Clin Oncol. (2001); 20: Abstract 1565.

Lipworth, A.D. et al., "Hand-foot syndrome (hand-foot skin reaction, palmar-plantar erthrodysesthesia): focus on sorafenib and sunitinib", Oncology, 2009, vol. 77, No. 5, pp. 257-271.

Nagore, E. et al., "Antineoplastic Therapy-Induced Palmar-Plantar Erythrodysesthesia ('Hand-Foot') Syndrome", Am J. Clin Dermatol. (2000), vol. 1, No. 4, pp. 224-234.

Porta, C. et al., "Allopurinol mouthwashes in the treatment of 50 fluorouracil-induced stomatitis", American Journal of Clinical Oncology, 1994, vol. 17, No. 3, pp. 246-247.

Porta, C. et al., "Uncovering Pandora's vase: the growing problem of new toxicities from novel anticancer agents. The case of sorafenib and sunitinib", Clinical and Experimental medicine, 2007, vol. 7, No. 4, pp. 127-134.

Robert, C. et al., "Cutaneous side-effects of kinase inhibitors and blocking antibodies", Lancet Oncology, 2005, nol. 6, No. 7, pp. 491-500.

Robert, C. et al., "Dermatologic symptoms associated with the multikinase inhibitor sorafenib", Journal of the American Academy of Dermatology, 2009, vol. 60, No. 2, pp. 299-305.

Rosenbaum, S.E. et al., "Dermatological reactions to the multitargeted tyrosine kinase inhibitor sunitinib", Supportive Care in Cancer, 2008, vol. 16, No. 6, pp. 557-566.

Tsavaris, N., "Decreased Oral Toxicity with the Local Use of Allopurinol in Patients W ho Received High Dose 5-Fluorouracil", Selective Cancer Therapeutics, 1991, vol. 7, No. 3, pp. 113-117.

Tsavaris, N. et al., "Concomitant Administration of 4 Hydroxypyrazolopyrimidine Allopurinol and High-Dose Continuous Infusion 5 Flurouracil" Oncology (Basel), vol. 47, No. 1, 1990, pp. 70-74, XP009075852 ISSN:0030-2414.

Van der Meer, "10th World Congress on Gastrointestinal Cancer", Lancet Oncology, 2008, vol. 9, No. 8, p. 709.

Webster-Gandy, J.D., "Palmar-plantar erythrodysesthesia (PPE): A literature review with commentary on experience in a cancer centre", European Journal of Oncology Nursing, 2007, vol. 11, No. 3, pp. 238-246.

Wilkes, G.M., "Palmar-Planter Erythrodysesthesia", Clinical J. Oncol. Nursing, 2005, vol. 9, No. 1, pp. 103-106.

Wood, L.S. et al., "Practical considerations in the management of hand-foot skin reaction caused by multikinase inhibitors", Community Oncology, 2010, vol. 7, No. 1, pp. 23-29.

Woolley, P.V., "A controlled trial of the effect of 4-hydroxypyrazolopyrimidine (allopurinol) on the toxicity of a single bolus dose of 5-fluorouracil", J. Clin Oncol., 1985, vol. 3, No. 1, pp. 103-109.

Yang, C-H. et al., "Hand-foot skin reaction in patients treated with sorafenib: a clinicopathological study of cutaenous manifestations due to multitargeted kinase inhibitor therapy", British Journal of Dermatology, 2008, vol. 158, No. 3, pp. 592-596.

European Search Report issued by the International Searching Authority (ISA/O.E.P.M.) on Dec. 18, 2006 in connection with International Application No. PCT/EP2006/011432.

International Search Report issued by the International Searching Authority (ISA/O.E.P.M.) on Oct. 8, 2007 in connection with International Application No. PCT/EP2007/055367.

International Search Report issued by the International Searching Authority (ISA/O.E.P.M.) on Jun. 29, 2010 in connection with International Application No. PCT/EP2010/055806.

written Opinion issued by the International Searching Authority (ISA/O.F.P.M.) on Jul. 7, 2010 in connection with International Application No. PCT/EP2010/055806.

Reply to PCT Written Opinion filed at the European Patent Office in connection with International Application No. PCT/EP2010/055806 on Feb. 28, 2011.

International Preliminary Report on Patentability (IPRP), issued on Apr. 15, 2011 in connection with PCT/EP2010/055806.

Response to International Preliminary Report on Patentability (IPRP), filed at the European Patent Office on Jun. 22, 2012 in connection with EP 10719314.

* cited by examiner

US 8,623,878 B2

USE OF ALLOPURINOL FOR THE TREATMENT OF HAND FOOT SKIN REACTION

This application claims benefit of U.S. Provisional Application No. 61/214,894, filed Apr. 29, 2009 and claims priority of European Patent Application No. EP 09 382 058.7, filed Apr. 29, 2009, and. The contents of all of the referenced applications are hereby incorporated by reference into the present application.

FIELD OF THE INVENTION

The present invention relates to the field of therapy, especially in oncology. It relates to the use of allopurinol or its pharmaceutically acceptable salts for the treatment or prevention of Hand-Foot Skin Reaction (HFSR) induced by Multi-targeted Kinase Inhibitors (MKI). It also relates to methods for the treatment of HFSR.

BACKGROUND OF THE INVENTION

Cancer is a group of diseases in which abnormal cells divide without control. Cancer cells can invade nearby tissues and can spread through the bloodstream and lymphatic system to other parts of the body. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system.

Several treatments are available for cancer, including surgery and radiation for localised disease, and drugs that destroy cancer cells (chemotherapy). Chemotherapy plays a significant part in cancer treatment, as it is required for the treatment of advanced cancers with distant metastasis and often helpful for tumour reduction before surgery (neoadjuvant therapy). It is also used following surgery or radiation (adjuvant therapy) to destroy any remaining cancer cells or prevent recurrence of the cancer.

Many anti-cancer drugs have been developed based on various modes of action: alkylating agents that act directly on the DNA (such as cisplatin, carboplatin, oxaliplatin, busulfan, chlorambucil, cyclophosphamide, ifosfamide, dacarbazine); antimetabolites that interfere with DNA and RNA synthesis (such as 5-fluorouracil, capecitabine, 6-mercaptopurine, methotrexate, gemcitabine, cytarabine (ara-C), fludarabine); anthracyclines that interfere with enzymes involved in DNA replication (such as daunorubicin, doxorubicin, epirubicin, idarubicin, mitoxantrone); microtubule disrupters (taxanes such as paclitaxel and docetaxel or Vinca alkaloids such as vinblastine, vincristine, and vinorelbine); topoisomerase inhibitors (such as etoposide, doxorubicin, topotecan and irinotecan); hormone therapy (such as tamoxifen, flutamide) and recently introduced targeted therapy (such as the inhibitors of EGFR cetuximab, gefitinib or the protein tyrosine kinase inhibitor imatinib), are the most frequently used.

The development of chemotherapy in the last decades has significantly improved the treatment of cancer, resulting in effective treatments in some types of cancers, and improved survival or time to progression in others. Currently, most chemotherapy is administered intravenously; however, oral chemotherapy drugs are gaining wider use.

Unfortunately, most chemotherapy drugs cannot differentiate between a cancer cell and a healthy cell. Therefore, chemotherapy often affects the body's normal tissues and organs which results in complication of treatments, or side effects. In addition to the problems they cause, side effects can prevent doctors from delivering the prescribed dose of chemotherapy, reducing the probability of a correct treatment of cancer. Most frequent side effects of chemotherapy are anaemia, neutropaenia, thrombocytopaenia, fatigue, alopecia, nausea and vomiting, mucositis and pain.

One the side effects associated with some chemotherapeutic agents, especially with 5-fluorouracil and its prodrug capecitabine, is Palmar-Plantar Erythrodysesthesia (PPE), an erythematous eruption of the palms and soles also known as Hand Foot Syndrome (HFS). PPE is a distinctive and relatively frequent toxic reaction. It is a painful swelling and erythematous rash, located in the palms and soles, often preceded by dysesthesia, usually in the form of a tingling sensation, and often associated with oedema. The rash may become bollous and then desquamate without scarring, and pain gradually increases. Erythema may also occur in periungal areas. Generally it is confined to the hands and feet, the hands are usually more severely affected than the feet.

Histologically PPE shows mild spongiosis, scattered necrotic and dyskeratotic keratynocites and vacuolar degeneration of the basal layer. Dermal changes in most cases include dilated blood vessels, papillary edema, and a sparse superficial perivascular limphohistiocytic infiltrate that can be found in varying degrees in the epidermis.

PPE is clearly distinct from other adverse skin reactions and is reviewed in Nagore E. et al, *Am J Clin Dermatol*. 2000, 1(4), 225-234. Despite its frequency, little is known of its causes.

The advent of molecularly targeted therapies has changed the face of cancer treatment in the last few years. Among the targeted therapies for cancer, there has been a keen interest in developing agents that interfere with angiogenesis, the process by which new blood vessels are formed. By blocking the activity of receptors such as the platelet derived growth factor (PDGFR) or the vascular endothelial growth factor receptor (VEGFR), or by inhibiting members of their signalling pathways, tumour vessel formation can be halted and even reversed. Some of these targets are the ubiquitous mitogen-activated protein kinase (MAPK) pathway or Raf/MEK/ERK pathway, which controls the growth and survival of human tumours in proangiogenic pathways, which also involve signalling through MAPK. Solid tumours frequently exhibit activating oncogenic mutations in ras and/or overactivation of Raf-1 kinase, resulting in dysregulated signaling through the MAPK pathway, and consequent tumor cell proliferation and angiogenesis.

This rational approach to cancer treatment lead to the development of a second generation tyrosine kinase inhibitors that are able to target more that one target and pathways. Agents targeting multiple pathways in tumour growth are highly attractive, potentially offering the benefits of combined therapy within a single agent. The majority of these newer agents inhibit more than one receptor tyrosine kinase and may have unique inhibition profiles. Among the multi-targeted kinase inhibitors (MKI's), sorafenib and sunitinib are already authorised for use, and vandetanib, motesanib, ABT-869 and several other compounds are still under development.

Sorafenib (Nexavar®) is an oral drug capable of inhibiting several receptor tyrosine kinases that are involved in tumour progression and angiogenesis. Sorafenib blocks Raf gene products (serine-threonine kinases), including mutated B-Raf, as well as platelet-derived growth factor-beta (PDGFR-β), FLt3, and vascular endothelial growth factor receptor-2 and -3 (VEGFR-2 and -3). Sorafenib has been approved by the FDA in 2005 and by the EMEA in 2006 for the treatment of metastatic renal cell carcinoma and advanced hepatocellular carcinoma.

Sunitinib (Sutent®) is also an oral drug, a multitargeted tyrosine kinase inhibitor that blocks VEGFR-1, -2, and -3, PDGFR-α and -β, Ret, c-Kit, and $FLT_3$. In 2006 it has been approved by the FDA and by the EMEA for use in patients with gastrointestinal stromal tumor (GIST) who are refractory to or intolerant of imatinib mesylate, and in patients with metastatic renal cell carcinoma. It is usually administered in a 4 week-on, 2 week-off schedule, to allow patients to recover from some potential toxicities.

The MKI's such as sorafenib and sunitinib have side effects, the most frequent being fatigue, hypertension, nausea and diarrhea. Their safety profiles are however generally more favorable than those of many standard chemotherapies.

However, as with other tyrosine kinase inhibitors, MKI's are associated with significant dermatologic adverse reactions. Hand-Foot Skin Reaction (HFSR) is the most clinically significant (Rosenbaum S E et al. *Support Care Cancer* (2008) 16:557-566 "Dermatological reactions to the multitargeted tyrosine kinase inhibitor sunitinib"; Robert C et al *J Am Acad Dermatol* 2009, vol. 60 no. 2, 299-305 "Dermatological symptoms associated with the multikinase inhibitor sorafenib").

Hand-Foot Skin Reaction (HFSR) is a distinct localized cutaneous reaction characterized by erythema, numbness, tingling and either dysesthesia or paresthesia, particularly on the palms and or soles. Histologically, it is characterized by thick, well defined hyperkeratotic lesions frequently affecting digital flexural location. It develops within the first 2-4 weeks of MKI administration. After several weeks the lesions, with or without blisters, are followed by areas of thickened or hyperkeratotic skin resembling skin calluses that are painful.

HFSR is described in: Lacouture M E et al. *The Oncologist* 2008, 13, no. 9, 1001-1011: "Evolving Strategies for the management of Hand-Foot Skin Reaction associated with the Multitargeted Kinase Inhibitors Sorafenib and Sunitinib"; Beldner M et al *The Oncologist* 2007 12:1178-1182 "Localized Palmar-Plantar epidermal hyperplasia: a previously undefined dermatological toxicity to sorafenib"; Yang C H et al. *British journal of Dermatology* 2008, 158 592-596 "Hand-Foot skin reaction in patients treated with sorafenib: a clinopathological study of cutaneous manifestations due to multitargeted kinase inhibitor therapy"; Porta C et al. *Clin Exp Med* 2007, 7:12-134 "Uncovering Pandora's vase: the growing problem of new toxicities from novel anticancer agents. The case of sorafenib and sunitinib"; Wood L. et al. *Community Oncology* 2010, vol. 7, no. 1 pages 23-29: "Practical Considerations in the Treatment of Hand Foot Skin Reaction caused by Multikinase Inhibitors".

As explained in these publications, Hand-Foot Skin Reaction is distinguished clinically and histologically from palmar plantar erythrodysestesia (PPE) [also known as Hand-foot syndrome (HFS)], induced by chemotherapy such as 5-FU, capecitabine, or pegylated liposomal doxorubicine.

Both conditions show palmar-plantar localization, tenderness, pain and resolution of the toxicity upon discontinuation of the drug.

However, the typical pattern of localized hyperkeratotic lesions surrounded by erythematous areas distinguishes HFSR from PPE, in which symmetric paresthesias, diffusely tender erythema and oedema occur. Further, HFSR can affect non pressure-bearing areas, such as toes and finger webs, and the lateral sides of the soles. Pathologically, MKI's induce keratinocyte vacuolar degeneration in the stratum malpighii together with epidermal acanthosis, while PPE induced by chemotherapy shows dermal-epidermal interface dermatitis and vacuolar degeneration of basilar keratynocytes. The main histologic changes observed in HFSR suggest a defect in cell maturation, with modifications in keratinocyte differentiation, possibly increased apoptosis of this same cell population, as well as a specific inflammation. The rate of epidermal cell replication is markedly accelerated in active lesions of HFSR. The most relevant histopathological characteristic of HFSR is keratinocyte damage, present as intracytoplasmic eosinophilic bodies, unique to this condition. The mechanism by which HFSR originates is not known.

The incidence of HFSR is high. A meta-analysis has shown that the summary incidence of HFSR in patients treated with sorafenib was 33.8% for grades 1-3, and 8.9% for grade 3 (Chu D., Lacouture M E et al. *Acta Oncologica* 2008; 4 16-186: "Risk of Hand Foot Skin Reaction with Sorafenib: A systematic Review and Meta-Analysis"). With sunitinib, the summary incidence was calculated at 18.9% for grades 1-3 and 5.5% for grade 3 (Chu D. Lacouture M E, et al. *Clinical Genitourinary Cancer* 2009, no. 1 11-19: "Risk of Hand Foot Skin Reaction with the Multitargeted Kinase Inhibitor Sunitinib in patients with Renal Cell and Non-Renal Cell carcinoma: a Meta-analysis"). HFSR can negatively affect health-related quality of life and activities of daily living in patients being treated with MKI's such as sorafenib and sunitinib.

The severity of HFSR is most widely done using the National Cancer Institute Common Terminology Criteria for Adverse Events (NCI-CTCAE v 3.0). The clinical characteristics of each grade are:

1. Minimal skin changes or dermatitis (e.g. erythema) without pain
2. Skin changes (e.g. peeling, blisters, bleeding, oedema) or pain; no interference with patient activities of daily living;
3. Ulcerative dermatitis or skin changes with pain; interferes with patients activities of daily living.

It can also be graded using modified criteria which better fit with clinical practice (Porta C et al. *Clin Exp Med* 2007, 7:12-134):

1. numbness, dysaesthesia, paraesthesia, tingling, painless swelling, erythema or discomfort of hands or feet, which does not disrupt patient's normal activities;
2. One or more of the following symptoms: painful erythema, swelling, hyperkeratosis of the hands or feet, discomfort affecting the patient's normal activities;
3. One or more of the following symptoms: moist desquamation, ulceration, blistering, hyperkeratosis, severe pain of the hands and feet, severe discomfort that causes the patient to be unable to work or perform daily activities.

There is at the moment no effective treatment for HFSR. Before treatment with MKI, removal of pre-existing hyperkeratotic areas and calluses is recommended. Once the skin reaction appears after initiating the treatment with MKI's, some of the few treatments that have been proposed are: cold compresses or ice packs, avoiding pressure on hands or feet; skin hydration; emollient skin creams, clobetasol ointment or topical analgesics. For the more severe grades (2-3), dose reduction or interruption of the treatment with MKI's is recommended. Urea, fluorouracil and tazarotene creams have also been mentioned, since these agents inhibit keratinocyte proliferation (Lacouture M E et al. *The Oncologist* 2008, vol. 13, no. 9, 1001-1011: "Evolving Strategies for the management of Hand-Foot Skin Reaction associated with the Multitargeted Kinase Inhibitors Sorafenib and Sunitinib", Anderson et al. *The Oncologist* 2009, vol. 14, no. 3, 291-302: "Search for evidence-based approaches for the prevention and palliation of Hand-foot Skin Reaction (HFSR) caused by the Multikinase Inhibitors"); Wood L. et al. *Community Oncology* 2010, vol. 7, no. 1 pages 23-29: "Practical Considerations in the Treatment of Hand Foot Skin Reaction caused by Multikinase Inhibitors").

None of the proposed treatments has yet been able to effectively treat or prevent HFSR. This is a serious problem for the patient, because besides the intrinsic discomfort and pain, in advanced grades it implies in a reduction or interruption of the chemotherapy with MKI's, which affects the survival and/or time to progression of the cancer being treated. It is clear that an effective treatment of HFSR is still needed, in order to untie the full potential of multikinase inhibitors and the different regimens and combinations in which they are and will be used.

Allopurinol is a structural isomer of hypoxanthine, it inhibits xanthine oxidase, an enzyme that converts oxypurines to uric acid. By blocking the production of uric acid, this agent decreases serum and urine concentrations of uric acid, thereby providing protection against uric acid-mediated end organ damage in conditions associated with excessive production of uric acid. It has been used for many years for the treatment or prevention of gout, hyperuricemia and kidney stones, through oral or parenteral systemic administration.

Allopurinol has also been reported for the treatment of mucositis, a frequent chemotherapy- or radiation-induced damage to the rapidly dividing cells lining the mouth, throat and gastrointestinal (GI) tract. Allopurinol is used in the form of mouthwashes (dispersion in water) (Porta C. et al, *Am J clin Oncol.* 1994, Vol 17, no. 3, 246-247). An improved formulation for mouthwashes comprising allopurinol, carboxymethylcellulose and water is described in JP-3106817. Hanawa et al. in *Drug Dev Ind Pharm* 2004, 30(2) 151-161 describe another mouthwash comprising allopurinol, polyethyleneoxide and carrageenan. Kitagawa et al. in *J Radiation Research* 2008, vol. 49, no. 1, 49-54, describe that Allopurinol gel mitigates radiation-induced mucositis and dermatitis in rats. Dagher et al., *Canadian Journal of Hospital Pharmacy*, vol. 40, no. 5 1987, page 189, discloses the use of allopurinol mouthwash and vaginal 0.1% cream for the treatment of 5-FU induced mucositis.

WO94/05293 and WO94/05291 describe synergistic compositions comprising methylsuphonylmethane (MSM) and at least one of oxypurinol or allopurinol and their use for the treatment of skin conditions, diseases and injuries such as burns, dermatitis, hyperkeratosis, sun exposure, skin ageing, etc. Oxypurinol and allopurinol are described as enhancing the skin healing or repairing properties of MSM.

W02007/138103 discloses and exemplifies the use of allopurinol, in particular topically in the form of a cream for the treatment of Palmar Plantar Erythrodysesthesia or Hand-Foot syndrome induced by fluoropyrimidine chemotherapy (5-FU and capecitabine). However, the skilled person knows that fluoropyrimidine and Multitargeted kinase inhibitors act at a molecular level by a very different mechanism, and their skin toxicities are different, both clinically and histologically, as discussed above.

Indeed, a interdisciplinary panel of experts in Wood et al. (*Community Oncology*) state at page 1 that:

"MKI-associated HFSR is a clinically and pathologically distinct skin toxicity from the HFS seen with older chemotherapeutic agents."

None of the cited documents mentions or suggests that allopurinol would be useful for the treatment or prevention of Hand-Foot Skin Reaction (HFSR).

SUMMARY OF THE INVENTION

The inventor has surprisingly found that allopurinol, when applied topically, in particular to the palms and soles of the patient, is very effective in the treatment and prevention of Hand Foot Skin Reaction (HFSR) induced by multitargeted kinase inhibitors (MKI). As show in the examples, topical application of allopurinol to cancer patients, being treated with MKI's and having developed this condition, completely eliminated the symptoms and avoided the further appearance of HFSR. This is more striking in the case of patients having developed the typical hyperkeratosis of HFSR, since it would be expected to be very difficult to topically treat the thick corneal layer present in the palms and soles, and also to reverse the process and bring the skin to a normal condition in a short period of time, with the disappearance of the hyperkeratosis, as shown in one of the examples.

Therefore, in one aspect the invention is directed to a medicament comprising allopurinol or a pharmaceutically acceptable salt thereof for use in the treatment or prevention of Hand Foot Skin Reaction induced by a multitargeted kinase inhibitor (MKI).

In a second aspect, the invention is directed to the use of allopurinol or a pharmaceutically acceptable salt thereof in the manufacture of a medicament in the treatment or prevention of Hand Foot Skin Reaction induced by a multitargeted kinase inhibitor.

In a third aspect, the invention is directed to a method for treating or preventing Hand Foot Skin Reaction induced by a multitargeted kinase inhibitor in a patient affected or likely to be affected by this condition, comprising topically applying a therapeutically effective amount of allopurinol or a pharmaceutically acceptable salt thereof.

Further embodiments of the invention are defined in the claims.

DETAILED DESCRIPTION OF THE INVENTION

As used herein, the term "multi-targeted receptor tyrosine kinase inhibitor" refers to a compound having a receptor binding profile exhibiting selectivity for multiple receptors shown to be important in angiogenesis.

In the context of the present invention, the term "Hand Foot Skin Reaction" (HFSR) defines the side effect to the skin of hands and feet of a cancer patient being treated with a multi-targeted receptor tyrosine kinase inhibitor. Their clinical and histological characteristics, and its grading are described above. As explained, it is different from Palmar-Plantar erythrodysesthesia (PPE), also known as Hand-Foot Syndrome (HFS), induced by other chemotherapeutic agents such as 5-FU and Capecitabine.

In the context of the present invention the term allopurinol refers also to the different tautomers of the compound, since it is a tautomeric mixture of 1H-pyrazolo[3,4-d]pyrimidin-4-ol and 1,5-dihydro-4H-pyrazolo[3,4-d]pyrimidin-4-one:

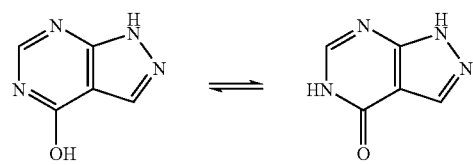 [SMILES: Oc1ncnc2[nH]ncc12 ; O=c1[nH]cnc2[nH]ncc12]

As mentioned above, the topical application of allopurinol or one of its pharmaceutically acceptable salts has surprisingly been found to be useful for the treatment and prevention of HFSR induced by MKI.

Thus, in one aspect the invention is directed to use of allopurinol or a pharmaceutically acceptable salt thereof in the manufacture of a medicament for the treatment or prevention of HFSR induced by Multitargeted Kinase Inhibitor therapy.

In one embodiment the medicament is in the form of a cream. Preferably the cream is a hydrophilic cream.

In another embodiment the medicament is for the treatment of HFSR induced by the MKI sorafenib, either alone or in combination with other agents.

In another embodiment the medicament is for the treatment of HFSR induced by the MKI sunitinib, either alone or in combination with other agents.

The medicament is thus useful for the treatment of patients suffering from cancer, preferably from renal cell carcinoma, hepatocellular carcinoma, breast cancer, gastrointestinal stromal tumors (GIST), non-small cell lung cancer (NSCLC), melanoma, and that are receiving MKI therapy, either as adjuvant, neoadjuvant or palliative. Examples of patients and therapies inducing HFSR have been discussed in the section "background of the invention".

The medicament containing Allopurinol for the treatment of HFSR is particularly useful in patients receiving or about to receive sorafenib, sunitinib, or other MKI's, either alone or in combination with other agents.

Local application of allopurinol allows an effective targeting of the affected areas, and avoids the toxicities and complications that systemic allopurinol can provoke in cancer patients. It avoids interfering with the cancer therapy.

Allopurinol is a compound very slightly soluble in water and alcohol; practically insoluble in chloroform and in ether; it dissolves in dilute solutions of alkali hydroxides.

It can be used as such, or, to improve the solubility in water, a salt such as the sodium salt can be used instead of the base.

In a preferred embodiment, the medicament is in the form of a topical pharmaceutical composition for the treatment of the hands and feet, comprising allopurinol or a pharmaceutically acceptable salt thereof, together with at least one topically acceptable carrier material.

In the topical compositions used to treat HFSR, allopurinol or its salt is typically present in an amount of from about 1 up to 10%, in particular from 1-8%, more particularly from 1-6%, especially from 1 up to 5%. Concentrations of about 1%, about 3% and about 8% are preferred.

A preferred range is from 2 up to 5%, more preferably from 2-4% of the total composition on a weight basis. An amount of about 3% has given good results and is especially preferred. All percentages given are weight-% (w/w), if not indicated otherwise.

Pharmaceutical compositions suitable for topical administration to the hands and feet, more preferably to the affected areas of the palms and soles, are for example creams, lotions, ointments, microemulsions, fatty ointments, gels, emulsion-gels, pastes, foams, tinctures, solutions, patches, bandages and transdermal therapeutic systems. Most preferred are creams or emulsion-gels.

Creams or lotions are oil-in-water emulsions. Oily bases that can be used are fatty alcohols, especially those containing from 12 to 18 carbon atoms, for example lauryl, cetyl or stearyl alcohol, fatty acids, especially those containing from 10 to 18 carbon atoms, for example palmitic or stearic acid, fatty acid esters, e.g. glyceryl tricaprilocaprate (neutral oil) or cetyl palmitate, liquid to solid waxes, for example isopropyl myristate, wool wax or beeswax, and/or hydrocarbons, especially liquid, semi-solid or solid substances or mixtures thereof, for example petroleum jelly (petrolatum, Vaseline) or paraffin oil. Suitable emulsifiers are surface-active substances having predominantly hydrophilic properties, such as corresponding non-ionic emulsifiers, for example fatty acid esters of polyalcohols and/or ethylene oxide adducts thereof, especially corresponding fatty acid esters with (poly)ethylene glycol, (poly)propylene glycol or sorbitol, the fatty acid moiety containing especially from 10 to 18 carbon atoms, especially partial glycerol fatty acid esters or partial fatty acid esters of polyhydroxyethylene sorbitan, such as polyglycerol fatty acid esters or polyoxyethylene sorbitan fatty acid esters (Tweens), and also polyoxyethylene fatty alcohol ethers or fatty acid esters, the fatty alcohol moiety containing especially from 12 to 18 carbon atoms and the fatty acid moiety especially from 10 to 18 carbon atoms, such as polyhydroxyethyleneglycol fatty acid ester (for example Tagat S), or corresponding ionic emulsifiers, such as alkali metal salts of fatty alcohol sulfates, especially having from 12 to 18 carbon atoms in the fatty alcohol moiety, for example sodium lauryl sulfate, sodium cetyl sulfate or sodium stearyl sulfate, which are usually used in the presence of fatty alcohols, for example cetyl alcohol or stearyl alcohol. Additives to the aqueous phase are, inter alia agents that prevent the creams from drying out, for example humectants, such as polyalcohols, such as glycerol, sorbitol, propylene glycol and/or polyethylene glycols, and also preservatives, perfumes, gelling agents, etc.

Ointments are water-in-oil emulsions that contain up to 70%, but preferably from approximately 20% to approximately 50%, water or aqueous phase. Suitable as fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax or beeswax. Emulsifiers are corresponding lipophilic substances, for example of the type indicated above, such as sorbitan fatty acid esters (Spans), for example sorbitan oleate and/or sorbitan isostearate. Additives to the aqueous phase are, inter alia humectants, such as polyalcohols, for example glycerol, propylene glycol, sorbitol and/or polyethylene glycol, and also preservatives, perfumes, etc.

Microemulsions are isotropic systems based on the following four components: water, a surfactant, for example a tensioactive, a lipid, such as a non-polar or polar oil, for example paraffin oil, natural oils such as olive or maize oil, and an alcohol or polyalcohol containing lipophilic groups, for example 2-octyldodecanol or ethoxylated glycerol or polyglycerol esters. If desired, other additives may be added to the microemulsions. Microemulsions have micelles or particles with sizes below 200 nm and are transparent or translucid systems, the form spontaneoulsy and are stable.

Fatty ointments are water-free and contain as base especially hydrocarbons, for example paraffin, petroleum jelly and/or liquid paraffins, also natural or partially synthetic fat, such as fatty acid esters of glycerol, for example coconut fatty acid triglyceride, or preferably hardened oils, for example hydrogenated groundnut oil, castor oil or waxes, also fatty acid partial esters of glycerol, for example glycerol mono- and di-stearate, and also, for example, the fatty alcohols increasing the water-absorption capacity, emulsifiers and/or additives mentioned in connection with the ointments.

With gels, a distinction is made between aqueous gels, water-free gels and gels having a low water content, which gels consist of swellable, gel-forming materials. There are used especially transparent hydrogels based on inorganic or organic macromolecules. High molecular weight inorganic components having gel-forming properties are predominantly water-containing silicates, such as aluminium silicates, for example bentonite, magnesium aluminium silicates, for example Veegum, or colloidal silicic acid, for example Aerosil. As high molecular weight organic substances there are used, for example, natural, semisynthetic or synthetic macromolecules. Natural and semi-synthetic polymers are derived, for example, from polysaccharides containing a great variety of carbohydrate components, such as celluloses, starches, tragacanth, gum arabic and agar-agar, and gelatin, alginic acid and salts thereof, for example sodium alginate, and derivatives thereof, such as lower alkylcelluloses, for example methyl- or ethyl-cellulose, carboxy- or hydroxy-lower alkylcelluloses, for example carboxymethyl- or hydroxyethyl-cellulose. The components of synthetic gel-forming macromolecules are, for example, suitably substituted unsaturated aliphatic compounds such as vinyl alcohol, vinylpyrrolidine, acrylic or methacrylic acid.

Emulsion-gels—also called "emulgels"—represent topical compositions which combine the properties of a gel with those of an oil-in-water emulsion. In contrast to gels, they contain a lipid phase which due to its fat-restoring property enables the formulation to be massaged in whilst, at the same time, the direct absorption into the skin is experienced as a pleasant property. Furthermore, one can observe an increased solubility for lipophilic active ingredients. One advantage of emulsion-gels over oil-in-water emulsions resides in the enhanced cooling effect which is brought about by the coldness due to evaporation of the additional alcohol component, if present.

Foams are administered, for example, from pressurised containers and are liquid oil-in water emulsions in aerosol form; un-substituted hydrocarbons, such as alkanes, for example propane and/or butane, are used as propellant. As oil phase there are used, inter alia hydrocarbons, for example paraffin oil, fatty alcohols, for example cetyl alcohol, fatty acid esters, for example isopropyl myristate, and/or other waxes. As emulsifiers there are used, inter alia, mixtures of emulsifiers having predominantly hydrophilic properties, such as polyoxyethylene sorbitan fatty acid esters (Tweens), and emulsifiers having predominantly lipophilic properties, such as sorbitan fatty acid esters (Spans). The customary additives, such as preservatives, etc., are also added.

Tinctures and solutions generally have an ethanolic base, to which water may be added and to which there are added, inter alia, polyalcohols, for example glycerol, glycols and/or polyethylene glycol, as humectants for reducing evaporation, and fat-restoring substances, such as fatty acid esters with low molecular weight polyethylene glycols, propylene glycol or glycerol, that is to say lipophilic substances that are soluble in the aqueous mixture, as a replacement for the fatty substances removed from the skin by the ethanol, and, if necessary, other adjuncts and additives. Suitable tinctures or solutions may also be applied in spray form by means of suitable devices. In this case, due to the solubility problems of allopurinol, a salt is more appropriate for tinctures or solutions.

Transdermal therapeutic systems with—in particular—local delivery of allopurinol contain an effective amount allopurinol optionally together with a carrier. Useful carriers comprise absorbable pharmacological suitable solvents to assist passage of the active ingredient through the skin. Transdermal delivery systems are, for example, in the form of a patch comprising (a) a substrate (=backing layer or film), (b) a matrix containing the active ingredient, optionally carriers and optionally (but preferably) a special adhesive for attaching the system to the skin, and normally (c) a protection foil (=release liner). The matrix (b) is normally present as a mixture of all components or may consist of separate layers.

All these systems are well known to the person skilled in the art. The manufacture of the topically administrable pharmaceutical preparations is effected in a manner known per se, for example by dissolving or suspending allopurinol in the base or, if necessary, in a portion thereof.

The compositions may also comprise conventional additives and adjuvants for dermatological applications, such as preservatives, especially paraben esters like methylparaben, ethylparaben, propylparaben, butylparaben, or quaternary ammonium compounds like benzalkonium chloride, or formaldehyde donors like imidazonidinyl urea, or alcohols like benzyl alcohol, phenoxyethanol or acids like benzoic acid, sorbic acid; acids or bases used as pH buffer excipients; antioxidants, especially phenolic antioxidants like hydroquinone, tocopherol and derivatives thereof, as well as flavonoids, or miscellaneous antioxidants like ascorbic acid, ascorbyl palmitate; perfumes; fillers such as kaolin or starch; pigments or colorants; UV-screening agents; moisturizers, especially glycerin, butylen glycol, hexylen glycol, urea, hyaluronic acid or derivatives thereof; anti-free radical agents such as vitamin E or derivatives thereof; penetration enhancers especially propylene glycol; ethanol; isopropanol; dimethylsulfoxide; N-methyl-2-pyrrolidone; fatty acids/alcohols such as oleic acid, oleyl alcohol; terpenes such as limonen, menthol, 1-8 cineole; alkyl esters such as ethyl acetate, butyl acetate; ion pairing agents such as salicylic acid.

Further details concerning suitable topical formulations may be obtained by reference to standard textbooks such as Banker and Rhodes (Ed) *Modern Pharmaceutics* $4^{th}$ ed. (2002) published by Marcel Dekker Inc.; *Harry's Cosmetology* (2000), 8th Edition, Chemical Publishing Co.: *Remington's Pharmaceutical Sciences* $20^{th}$ ed Mack Publishing Co. (2000).

In a preferred embodiment allopurinol is formulated as a cream, preferably in an emollient base provided the emollient base is suitable for topical application on the skin, is substantially non-toxic and provides a suitable carrier for allopurinol or its pharmaceutically acceptable salts. A properly chosen emollient base may also provide a certain amount of relief in itself. In a particular case, a moisturizing cream is preferred as a base.

Emollients may be e.g. fatty alcohols, hydrocarbons, triglycerides, waxes, esters, silicone oils and lanolin containing products. Fatty alcohols are e.g. cetyl alcohol, octyldodecanol, stearyl alcohol and oleyl alcohol. Hydrocarbons include mineral oil, petrolatum, paraffin, squalene, polybutene, polyisobuten, hydrogenated polyisobutene, cerisin and polyethylene. Triglycerides are e.g. castor oil, caprylic/capric triglyceride, hydrogenated vegetable oil, sweet almond oil, wheat germ oil, sesame oil, hydrogenated cottonseed oil, coconut oil, wheat germ glycerides, avocado oil, corn oil, trilaurin, hydrogenated castor oil, shea butter, cocoa butter, soybean oil, mink oil, sunflower oil, safflower oil, macadamia nut oil, olive oil, apricot kernel oil, hazelnut oil and borage oil. Waxes include e.g. carnauba wax, beeswax, cadelilla wax paraffin, Japan wax, microcrystalline wax, jojoba oil, cetyl esters wax, and synthetic jojoba oil. Esters include e.g. isopropyl myristate, isopropyl palmitate, octyl palmitate, isopropyl linoleate, 12-15 alcohol benzoates, cetyl palmitate, myristyl myristate, myristyl lactate, cetyl acetate, propylene glycoldicaprylate/caprate, decyl oleate, stearyl heptanoate, diisostearyl malate, octylhydroxystearate and isopropyl isostearate. Silicone oils are e.g. dimethicone (dimethyl polysiloxane) and cyclomethicone. Lanolin containing products are e.g. lanolin, lanolin oil, isopropyl lanolate, acetylated lanolin alcohol, acetylated lanolin, hydroxylated lanolin, hydrogenated lanolin and lanolin wax.

In a preferred embodiment allopurinol is prepared by mixing it with a commercial basic cream, such as Bag Balm or Basiscreme DAC (Deutsches Arzneimittel codex).

The daily dosage of the topical formulation comprising allopurinol or its pharmaceutically acceptable salts may depend on various factors, such as sex, age, weight and individual condition of the patient, as well as the chemotherapy he is being or will be given and the severity of the HFSR.

The topical pharmaceutical compositions, e.g. in the form of creams, emulsion-gels or gels may be applied once, twice or three times daily, but also more frequent daily applications such as 5 to 10 times a day are possible provided that the symptoms of HFSR are eliminated or avoided. The dosage may be variable, in function of the severity of the HFSR symptoms, or the cycles or dosages of the MKI therapeutic treatment. One fingertip per hand or foot per application is recommended.

The pharmaceutical composition of the invention is administered to patients already suffering from HFSR in its different grades, or as a preventive treatment to patients susceptible to develop HFSR as a consequence of a MKI therapeutic treatment that is administered or about to be administered.

The administration can be intensified shortly before, during and after chemotherapeutic treatment, when the risks of developing HFSR are higher, and can be reduced during periods of rest between cycles.

The invention will be further illustrated by means of examples, they should no be taken as limiting the scope of the invention as defined by the claims.

EXAMPLES

Example 1

Preparation of a Topical Formulation Comprising Allopurinol

A formulation was prepared by suspending allopurinol base (3% by weight of total formulation) in 5% water and then adding Basiscreme DAC (92%) and mixing.

The composition of the Basic cream DAC is as follows:
Glycerolmonostearate: 4.0
Cetylalcohol 6.0
Medium chain triglyceride 7.5
White Vaseline 25.5
Polyoxyethylenglycerol monostearate 7.0
Propylenglycol 10.0
Water 40.0

The resulting cream is distributed in suitable containers and stored. The cream is easily applicable by the patients.

Example 2

Treatment of Hand Foot Skin Reaction

A male patient (65 y) having developed metastatic renal cell carcinoma (MRCC), was treated surgically and after progression of the metastasis he was treated with Nexavar® (sorafenib) as palliative therapy in a reduced dose (200 mg 2× daily). The therapy was interrupted due to HFSR, fatigue, loss of appetite and diarrhea after 7 months. A third line/second line palliative therapy was tried with Sutent® (sunitinib), at a reduced dosage of 37.5 mg daily for days 1-28 every 6 weeks.

The patient had developed HFSR during the treatment with sorafenib, with a very thick hyperkeratosis and pain to the palms and soles, which did not disappear with the change of medication from sorafenib to sunitinib. To try to improve his state and avoid interrupting the cancer therapy, topical treatment was nitrated with the cream prepared in example 1, administered 3 times daily.

Results: following the topical treatment with allopurinol, the symptoms of HFSR disappeared nearly completely and the therapy with sunitinib could be completed without any dose reduction or delay in the treatment due to HFSR. No toxics effects associated to the topical allopurinol treatment were observed.

Surprisingly, after only one week of treatment with allopurinol, the symptoms of HFSR reverted from grade 3 to grade 1 and 0 in most areas. Most significantly, the thick hyperkeratosis disappeared. The treatment with sunitinib and the allopurinol cream was continued until interruption of the treatment because of tumor progression.

Example 3

Treatment of Hand Foot Skin Reaction

A male patient (74 y) having developed Hepatocellular Carcinoma (HCC) started palliative therapy with sorafenib at a initial reduced dose (200 mg 2× daily). After 2½ months he had developed HFSR grade 1. He was treated with the allopurinol cream as described in example 1, and the HFSR symptoms disappeared in 7 days.

The sorafenib dosage was escalated to the recommended dose of 400 mg 2× daily. No further HFSR symptoms were appreciated, although other side effects such as diarrhea were present but manageable. The patient continued his treatment with sorafenib as planned.

Example 4

A male patient (56 y) with metastatic renal cell carcinoma (MRCC), was diagnosed in August 2008 with bone and lung metastasis. He was first treated with Torisel i.v. for 6 month. After progression of the metastasis and a nephrectomy of the right kidney he was treated with Sutent® (sunitinib) as palliative therapy in a standard dose of 50 mg daily at days 1-28 every 6 weeks.

The patient had developed HFSR during the treatment with sunitinib, with a keratosis (desquamation and lesions in the finger tips) and pain to the palms and soles, which did not disappear after treatment with emollient cream. To try to improve his state and avoid interrupting the cancer therapy, topical treatment was initiated with the allopurinol cream prepared in example 1, administered 3 times daily.

Results: following the topical treatment with allopurinol, the symptoms of HFSR nearly completely disappeared and the therapy with sunitinib could be completed without any dose reduction or delay in the treatment due to HFSR. No toxics effects associated to the topical treatment with allopurinol were observed.

After only one week of treatment with allopurinol, the symptoms of HFSR reverted from grade 2 to grade 1 and 0 in most areas. The treatment with sunitinib and allopurinol cream is still ongoing.

Example 5

A female patient (71 y) first diagnosed in 2001 with renal cell carcinoma was treated surgically. In 2005 she developed metastatic renal cell carcinoma (MRCC) (liver and local metastasis), and after progression of the metastasis she was treated with Nexavar® (sorafenib) as palliative therapy (400 mg 2× daily). The therapy was interrupted in September 2007 due to toxicity (HFSR, diarrhea). A second line palliative therapy was tried with Sutent® (sunitinib), at a dosage of 50 mg daily, at days 1-28 every 6 weeks. It had to be interrupted after 1 month due to bigger toxicity problems than with Nexavar (edema, depression, allergy), and changed back to Nexavar (sorafenib) therapy, which after one month was complemented with the allopurinol cream of example 1 and loperamide to treat HFSR and diarrhea. The therapy allowed a good control of the HFSR, but not diarrhea, for nearly two years (November 2007-September 2009). The treatment was interrupted after cancer progression. She was then treated during a short period of time with Afinitor (everolimus) 10 mg daily (September 2009-March 2010), which was interrupted in view of the lack of response and tumor progression. In the absence of alternative treatment Nexavar (sorafenib) at a reduced dosage was resumed in March 2010. Following development of HFSR the treatment was again complemented with the allopurinol cream one month later.

Results: following the topical treatment with allopurinol, the symptoms of HFSR disappeared nearly completely and the therapy with Nexavar could be continued. No toxics effects associated to the topical allopurinol treatment were observed.

As shown by the examples, with the four patients that had developed HFSR, the treatment with allopurinol improved their HFSR and allowed the completion of MKI therapy as planned.

The invention claimed is:

1. A method for treating Hand Foot Skin Reaction (HFSR) induced by Multitargeted Kinase (MKI) therapy in a patient in need thereof, comprising administering to the patient a medicament having an amount of allopurinol or a pharmaceutically acceptable salt thereof which is therapeutically effective to treat Hand Foot Skin Reaction.

2. The method according to claim 1, wherein the HFSR is induced by sorafenib.

3. The method according to claim 2, wherein the medicament is administered topically to the skin of the hands or feet.

4. The method according to claim 2, wherein the medicament comprises about 1% to about 10% by weight of the composition of allopurinol or a pharmaceutically acceptable salt thereof.

5. The method according to claim 4, wherein the medicament comprises about 1% to about 10% by weight of the composition of allopurinol or a pharmaceutically acceptable salt thereof.

6. The method according to claim 1, wherein the HFSR is induced by sunitinib.

7. The method according to claim 6, wherein the medicament is administered topically to the skin of the hands or feet.

8. The method according to claim 6, wherein the medicament comprises about 1% to about 5% by weight of the composition of allopurinol or a pharmaceutically acceptable salt thereof.

9. The method according to claim 8, wherein the medicament comprises about 1% to about 5% by weight of the composition of allopurinol or a pharmaceutically acceptable salt thereof.

10. The method according to claim 1, wherein the medicament is administered topically to the skin.

11. The method according to claim 10, wherein the medicament is administered topically to the skin of the hands or feet.

12. The method according to claim 11, wherein the medicament comprises about 1% to about 10% by weight of the composition of allopurinol or a pharmaceutically acceptable salt thereof.

13. The method according to claim 12, wherein the medicament comprises about 1% to about 5% by weight of the composition of allopurinol or a pharmaceutically acceptable salt thereof.

14. The method according to claim 13, wherein the medicament comprises about 3% by weight of the composition of allopurinol or a pharmaceutically acceptable salt thereof.

15. The method according to claim 1, wherein the medicament is a cream.

16. The method according to claim 15, wherein the medicament is a hydrophilic cream.

17. The method according to claim 1, wherein the medicament comprises about 1% to about 10% by weight of the composition of allopurinol or a pharmaceutically acceptable salt thereof.

18. The method according to claim 17, wherein the medicament comprises about 1% to about 5% by weight of the composition of allopurinol or a pharmaceutically acceptable salt thereof.

19. The method according to claim 18, wherein the medicament comprises about 3% by weight of the composition of allopurinol or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,623,878 B2 | Page 1 of 1 |
| APPLICATION NO. | : 12/770179 | |
| DATED | : January 7, 2014 | |
| INVENTOR(S) | : Rodemer | |

It is certified that error appears in the above-identified patent and that said Letters Patent is hereby corrected as shown below:

In the Claims:

In claim 5, at column 14, line 2: "10%" should read --5%--

In claim 8, at column 14, line 10: "5%" should read --10%--

Signed and Sealed this
Twenty-seventh Day of May, 2014

Michelle K. Lee
*Deputy Director of the United States Patent and Trademark Office*